(12) United States Patent
Pang et al.

(10) Patent No.: US 6,558,325 B1
(45) Date of Patent: May 6, 2003

(54) MEDICAL DIAGNOSTIC ULTRASONIC IMAGING METHOD AND SYSTEM FOR DISPLAYING MULTI-PHASE, MULTI-FRAME IMAGES

(75) Inventors: Linyong Pang, Stanford, CA (US); John A. Hossack, Charlottesville, VA (US)

(73) Assignee: Acuson Corporation, Mountain View, CA (US)

( * ) Notice: Subject to any disclaimer, the term of this patent is extended or adjusted under 35 U.S.C. 154(b) by 403 days.

(21) Appl. No.: 09/614,693

(22) Filed: Jul. 13, 2000

(51) Int. Cl.[7] .................................................. A61B 8/00
(52) U.S. Cl. ...................................................... 600/443
(58) Field of Search ................................ 600/437, 443, 600/447, 458, 515–518; 128/916

(56) References Cited

U.S. PATENT DOCUMENTS 5,315,512 A * 5/1994 Roth ........................... 600/443
5,817,022 A    10/1998 Vesely
5,976,088 A *  11/1999 Urbano et al. .............. 600/443
6,139,500 A *  10/2000 Clark .......................... 600/443
6,477,450 B2 *  9/2002 Olstad ........................ 600/437

* cited by examiner

Primary Examiner—Francis J. Jaworski

(57) ABSTRACT

A medical diagnostic ultrasonic imaging system acquires image data for at least two frames at each of multiple positions, each frame identified with a respective phase of a physiological cycle. A multiphase 3-D or extended field of view data set is constructed from the image data. Then a plurality of images are generated from the multiphase data set. Each image is associated with a respective phase of the physiological cycle, and these images are displayed in sequence to a user. The acquired sequence of image frames is synchronized by adding frames to the sequence in portions of the sequence characterized by a low number of image frames per period of the physiological cycle, and by removing image frames from portions of the sequence characterized by an excessive number of frames per period of the physiological cycle.

21 Claims, 7 Drawing Sheets

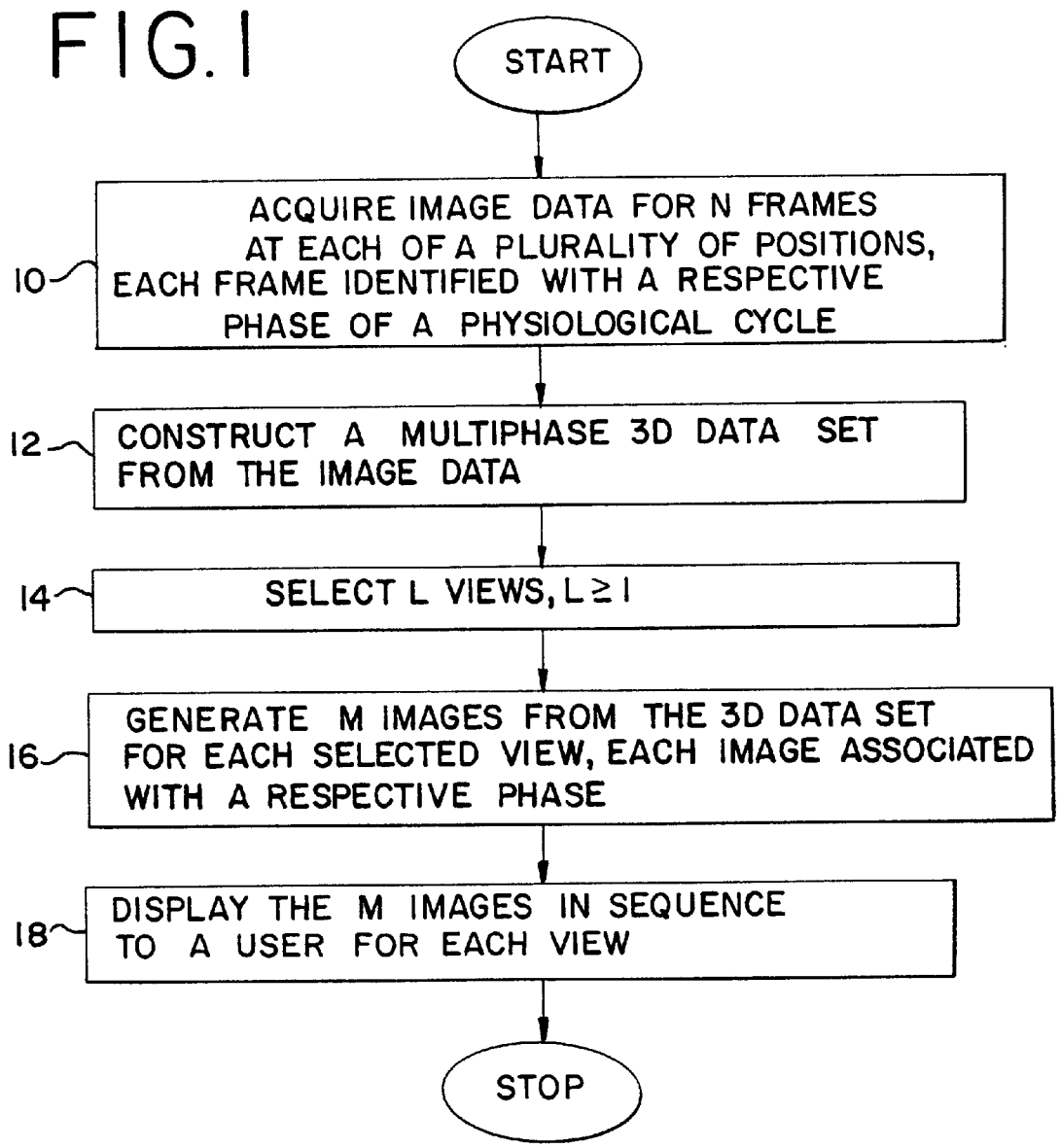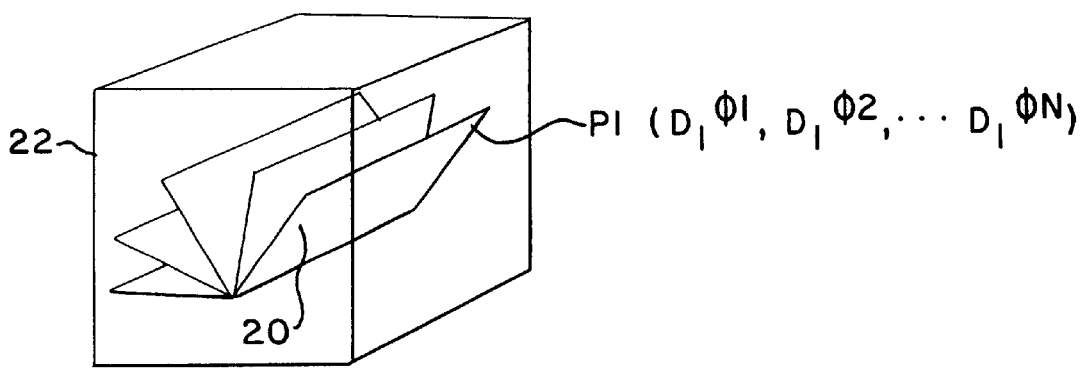

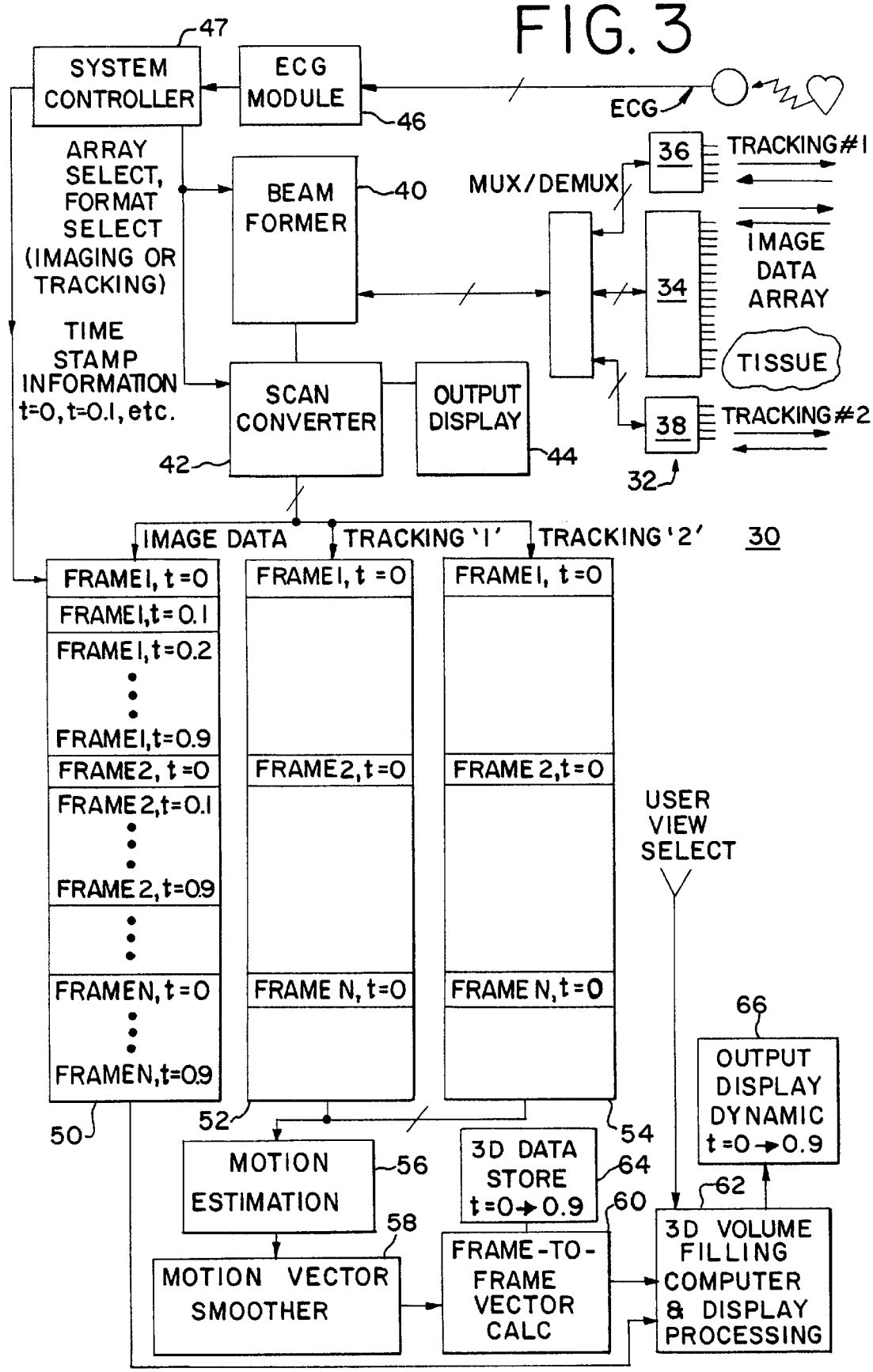

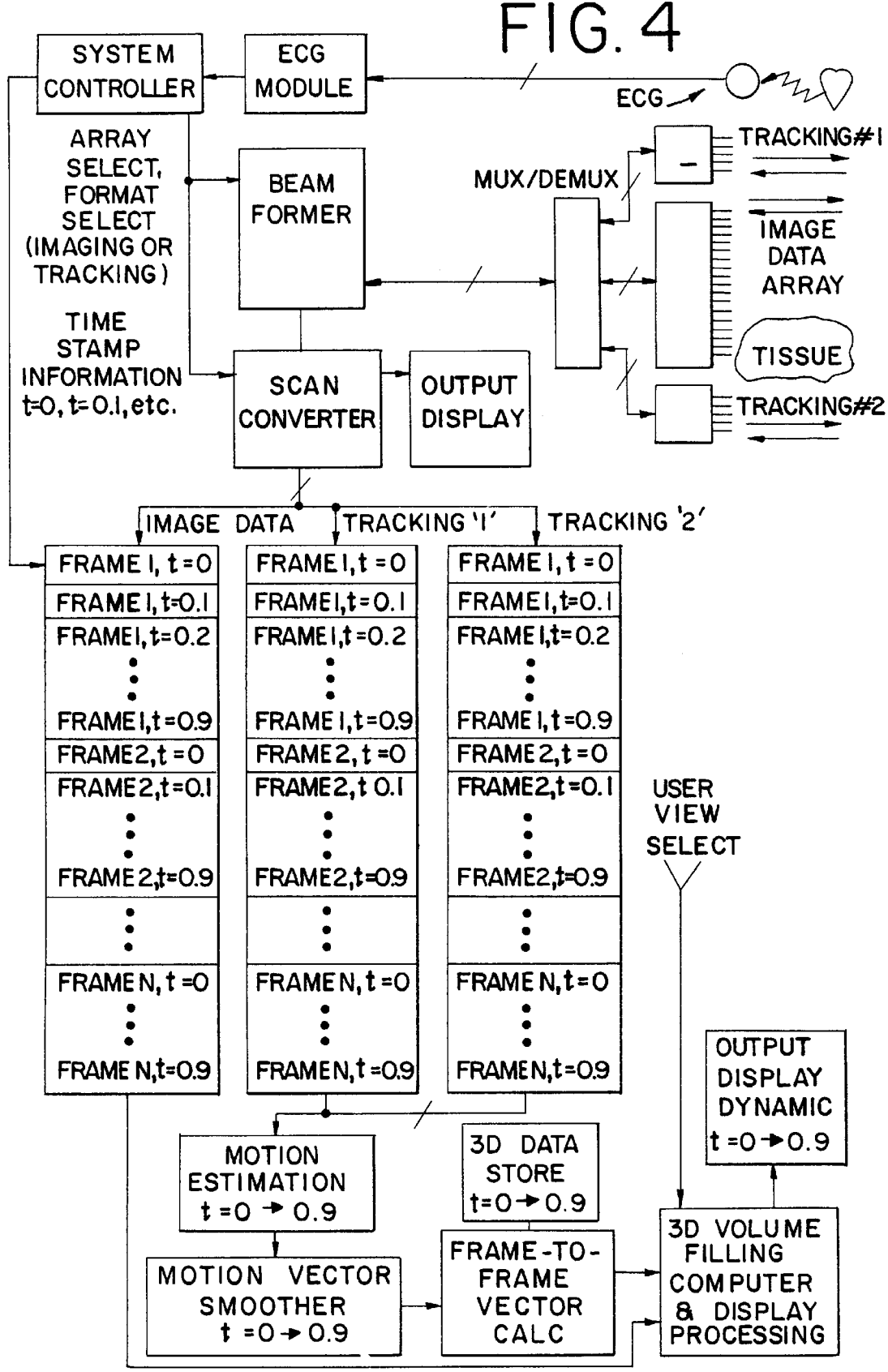

MEDICAL DIAGNOSTIC ULTRASONIC IMAGING METHOD AND SYSTEM FOR DISPLAYING MULTI-PHASE, MULTI-FRAME IMAGES

BACKGROUND

This invention relates generally to medical diagnostic ultrasonic imaging techniques, and in particular to such imaging techniques that provide multiple images displayed in sequence, wherein each image is associated with a respective phase of a physiological cycle.

U.S. Pat. No. 6,014,473, filed Aug. 22, 1997, discloses a system for collecting single frames of image data from each of a plurality of spatial locations. Tracking information is collected with each frame, and this tracking information is used to assemble the frames into a static three-dimensional image or an extended field of view image. In three-dimensional imaging, the transducer probe is swept across a three-dimensional volume, and the tracking data is obtained along tracking planes oriented generally transverse to the image planes. In extended field of view imaging, the transducer probe is maintained within a plane such that multiple image frames are obtained in the same plane. The tracking information is then used to reconstruct an extended (typically elongated) field of view from multiple ones of the coplanar images. In both cases, the three-dimensional image or the extended field of view image is a static image. The entirety of the above-identified U.S. Pat. No. 6,014,473 is hereby incorporated by its reference for its teaching of techniques for forming three-dimensional images and extended field of view images.

It is also known to acquire image frames from a particular part of the cardiac cycle. This can be done by triggering image acquisition at a specified time duration after a particular feature of the ECG signal, such as the R wave.

BRIEF SUMMARY

The present invention is defined by the following claims, and nothing in this section should be taken as a limitation on these claims.

A medical diagnostic ultrasonic imaging method for generating a multiple image sequence includes acquiring a sequence of medical ultrasonic image frames. This sequence includes $C_i$ frames in each $i^{th}$ period of a physiological cycle such as the cardiac cycle. An integer N is selected based on a function of selected values of $C_i$, e.g., maximum, minimum, average, median. At least one image frame is added to a portion of the sequence characterized by fewer than N frames per physiological cycle, and/or at least one image frame is removed from a portion of the sequence characterized by more than N frames per physiological cycle. Preferably, a cluster technique is used to determine the average physiological cycle period.

BRIEF DESCRIPTION OF THE DRAWINGS

FIG. 1 is a flow chart of a method that incorporates a first preferred embodiment of this invention.

FIG. 2 is a schematic diagram illustrating a multiphase 3-D data set created using the method of FIG. 1.

FIGS. 3 and 4 are schematic diagrams of alternative embodiments for practicing the method of FIG. 1.

DETAILED DESCRIPTION OF THE PRESENTLY PREFERRED EMBODIMENTS

Figure 5:
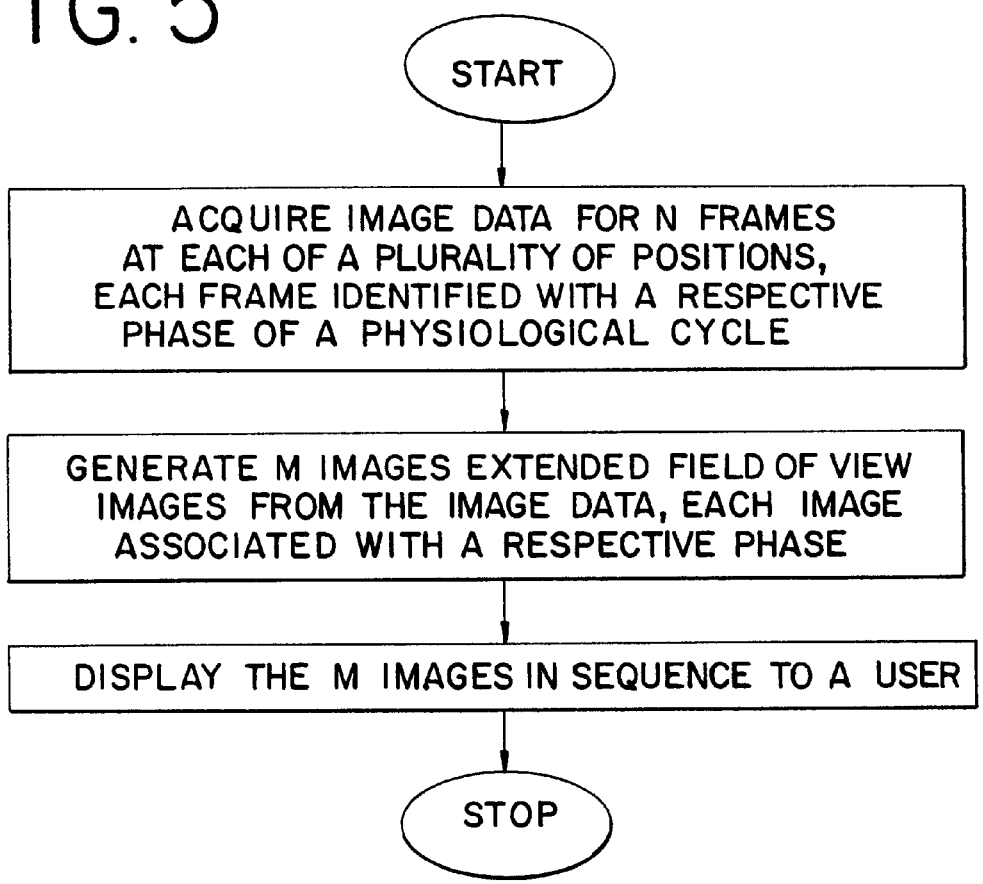
FIG. 5 is a flow chart of a method that incorporates a second preferred embodiment of this invention.

Turning now to the drawings, the method illustrated in FIG. 1 initially acquires image data for N frames at each of a plurality of transducer positions, wherein each frame is identified with a respective phase of a physiological cycle and N is greater than or equal to 2 (block 10). In one example, the image frames acquired in block 10 are each identified with a respective phase of an ECG signal. Typically, 10 to 25 frames of image data are acquired at each transducer position for each cardiac cycle. This represents a balance between computational requirements and adequate display of a moving image. For simplicity, the following example will consider the case where N equals 10, and 10 image data frames are collected for each transducer position. If the average ECG period is 1000 ms, this represents an interval of about 100 ms between consecutive frames of acquired image data. In general, it is preferable to acquire a large number of frames per heart cycle, but this will often lead to a large amount of data requiring a great deal of memory. The image data preferably comprises one or more of B-mode, color Doppler velocity, and color Doppler energy information.

In block 12 of the method of FIG. 1, the image data is used to construct a multiphase 3-D data set. That is, respective image data frames are associated with corresponding positions and phases with respect to a physiological cycle (e.g., the heart cycle as indicated by an ECG signal) in the 3-D data set.

FIG. 2 shows a schematic representation of the multiphase 3-D data set in which a plurality of frames 20 have been positioned within a three-dimensional volume 22. Each frame includes a plurality of data points, and the point P1 is indicated. P1 includes the data for point 1 for each of the N phases φ1 through φN, as schematically shown in FIG. 2.

In block 14 of FIG. 1, a series of L views is selected. L is an integer greater than zero, and the term "series" is intended broadly to cover one or more views. Typically, each view may be an arbitrarily positioned plane within a three-dimensional space. For example, each view may be slightly displaced from the previous view when L>1. Alternately, the selected view or views can be those appropriate for a surface rendering, a volume projection such as a maximum intensity projection, or multiple orthogonal slices.

In block 16, M images are generated from the 3-D data set for each of the selected views, each image associated with a respective phase with respect to a physiological signal. The same viewing calculation (e.g. extracting a two-dimensional view from the three-dimensional data set) is performed on the separate phases for each phase of the physiological cycle stored in the data set (10 in this example). This is repeated for all of the views.

In block 18, the M images for a given view are displayed in sequence to a user. This can be done by playing the M images sequentially on a video display at a frame rate equivalent to the acquisition rate. For example, if the phases are acquired at 100 ms intervals, then the output can be displayed at 100 ms intervals between consecutive frames.

Preferably, the user is provided with means (not shown) for directing the system to play the images back at a faster or slower rate if desired, or to pick out static frames from the sequence. Alternately, the user of the system can change the view while cycling through the M cardiac phases. The user will perceive a pulsating object while the view is changing.

FIG. 3 shows a block diagram of a medical diagnostic imaging system suitable for implementing the method of FIG. 1. The system illustrated in FIG. 3 is closely related to that disclosed in the above-identified U.S. Pat. No. 6,014,473, and that application should be consulted for further details of operation.

Briefly, the system 30 includes a transducer probe 32 having an image transducer array 34 and first and second tracking transducer arrays 36, 38. Preferably, the tracking transducer arrays 36, 38 are oriented at right angles to the image transducer array 34.

The transducer probe 32 is connected to a transmit/receive beamformer 40 which is in turn coupled to a scan converter 42 and an output display 44. An ECG module 46 provides a signal indicative of the ECG cycle to a system controller 48.

The system controller 48 controls the beamformer 40 and the scan converter 42 to generate image data that is stored in a memory 50 and tracking data that is stored in memories 52 and 54.

In this example 10 frames of image data are stored in the memory 50 for each spatial position of the transducer probe, and each frame is time stamped with the respective phase with respect to the heart cycle. Tracking data is stored in memories 52 and 54 only for the first frame of each set of frames associated with a single position. Typically, the first frame in each set (t=0 in FIG. 3) is phased to a stable portion of the heart cycle, such as 30 milliseconds after the R wave. Of course, instead of the first frame after the R wave, position information may be stored for any desired phase of the heart cycle.

A motion estimator 56 estimates frame-to-frame motion, using the techniques described at length in U.S. Pat. No. 6,014,473. In this case, one motion estimate determined from the selected phase is used for all phases of the cardiac cycle associated with the respective position. For example, all frames for position 1 are associated with the same estimate of motion that is determined for position 1 using the tracking data for t=0. This is believed to be a good approximation that saves a considerable amount of computational time. In some applications speckle may become decorrelated, and this may affect motion estimation accuracy. Therefore, in an alternate preferred embodiment, all frames are used to estimate motion. Motion estimates obtained by the motion estimator 56 are provided to a motion vector smoother 58, and the smoothed motion vectors are used to determine frame-to-frame vector motion in block 60. Computer 62 uses these frame-to-frame motion vectors to register the image data from the memory 50, as shown by way of example in FIG. 2. That is, the position information obtained from the block 60 is used to register the image data from the memory 50 by means of standard three-dimensional image interpolation. In this way the desired multiphase three-dimensional data set is constructed from the image data and is stored in the memory 64.

The user selects one or more views, and the computer 62 performs the necessary display processing to generate a plurality of images from the 3-D data set for each selected view, each image associated with the respective phase of the physiological cycle. These images are then displayed in sequence to a user on a display 66.

FIG. 4 shows an alternative, preferred embodiment that is similar to the embodiment of FIG. 3, except that the embodiment of FIG. 4 stores tracking data for frames of each phase. In this way tracking data is stored for all frames, not a subset of frames. The 3-D volume filling computer 62 creates a separate three-dimensional data set for each separate respective phase from the two-dimensional image frames associated with that phase, and the N separate 3-D data sets, taken together, can be considered a multi-phase 3-D data set. In other respects the embodiment of FIG. 4 operates similarly to that described above in conjunction with FIG. 3.

The foregoing discussion is related to three-dimensional data set embodiments of this invention. Other implementations of the invention relate to extended field of view imaging. As shown in FIG. 5, one preferred method acquires image data for N frames at each of a plurality of transducer positions, each frame identified with a respective phase of a physiological cycle. In this case the separate frames are coplanar. Next, M extended field of view images are generated from the image data, each image associated with a respective phase. Finally, the M images are presented in sequence to a user.

Figure 6:
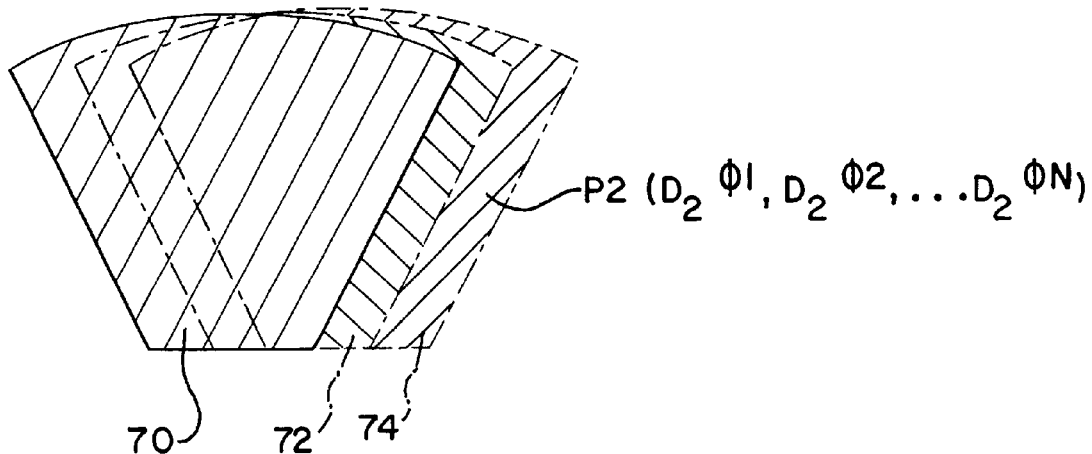
FIG. 6 is a schematic diagram of a multiphase extended field of view data set created using the method of FIG. 5.

FIG. 6 is a schematic diagram showing the manner in which three frames 70, 72, 74 are combined to produce an extended field of view. The cross-hatched fractions of the frame 72 and the frame 74 are combined with the cross-hatched portion of the frame 70 to produce an extended field of view that is elongated as compared to any one of the image frames. As shown in FIG. 6, the extended field of view data set is a multiphase data set in the sense that for each point, such as the point P2, image data is provided for each of N separate phases $\phi1, \phi2, \phi3, \ldots \phi N$.

This alternative embodiment can be implemented in a manner similar to that described above in conjunction with FIGS. 3 and 4. In this case, the tracking data (which may be obtained from the image data) is preferably obtained in the same plane as the image data. The computer 62 forms the extended field of view data set including image information for each of the selected phases of the physiological cycle. The computer 62 then generates a sequence of extended field of view images from the image data, each extended field of view image associated with the respective phase of the physiological cycle.

Of course, many alternatives are possible to the preferred embodiments described above. For example, in some ultrasound systems an ECG signal is not available. One alternative for extracting a cardiac time reference is to detect the frame in which maximum Doppler flow velocity or energy is detected, for example by summing all energy levels for all color pixels and then dividing by the number of color pixels to derive mean energy. In this approach it is preferable to use a fast acquisition rate for detecting the maximum Doppler flow rate (such as 20 frames per second or higher). Regardless of the frame rate that is used for the purpose of detecting the Doppler flow maximum, only a subset of frames is preferably used for generating the multiphase 3-D data set or the multiphase extended field of view data set.

In the foregoing discussion, for both 3-D multiphasic imaging and for 2-D extended field of view multiphasic imaging, N frames are acquired for each of the plurality of transducer positions, each frame corresponding to a body cycle phase. In the more general case, the transducer can be continually moved while N frames are acquired. Furthermore, the number of frames acquired for successive body cycles may be different. Since the time stamp for the beginning of the body cycle (R-wave, for example) and the time stamps for each acquired images are known using the previously described means, M images, each associated with a respective phase of the body cycle, can still be generated.

Furthermore, this invention is not limited to use with cardiac cycles. Rather, it is well suited for use with a wide variety of physiological cycles, including the respiratory cycle.

PREFERRED METHODS FOR ASSIGNING A PHASE TO ACQUIRED IMAGE FRAMES

The dynamic, multiphasic imaging described above is most useful when image frames of the same phase of the physiological cycle are combined to form each multi-frame image. Achieving this goal is complicated by the fact that physiological cycles such as the heart cycle generally have a period equal to a non-integer number of image frames, and such cycles are not perfectly regular. If image frames that are not matched in phase of the physiological cycle are combined in a multi-frame image, the composite image will appear banded and may appear to move from side to side in a completely non-physiologically correct manner.

The preferred method described below forces the desired synchronization. In dynamic color Doppler imaging, the duration of the systolic burst and its speed of flow are such that the systolic burst should appear simultaneously along the imaged length of a vessel or not at all. The preferred method achieves synchronization by adding or dropping image frames as appropriate during times of minimal flow velocities to achieve synchronization. Preferably, the displayed frame rate is adjusted if necessary to most closely match the estimated frame rate.

Figure 7:
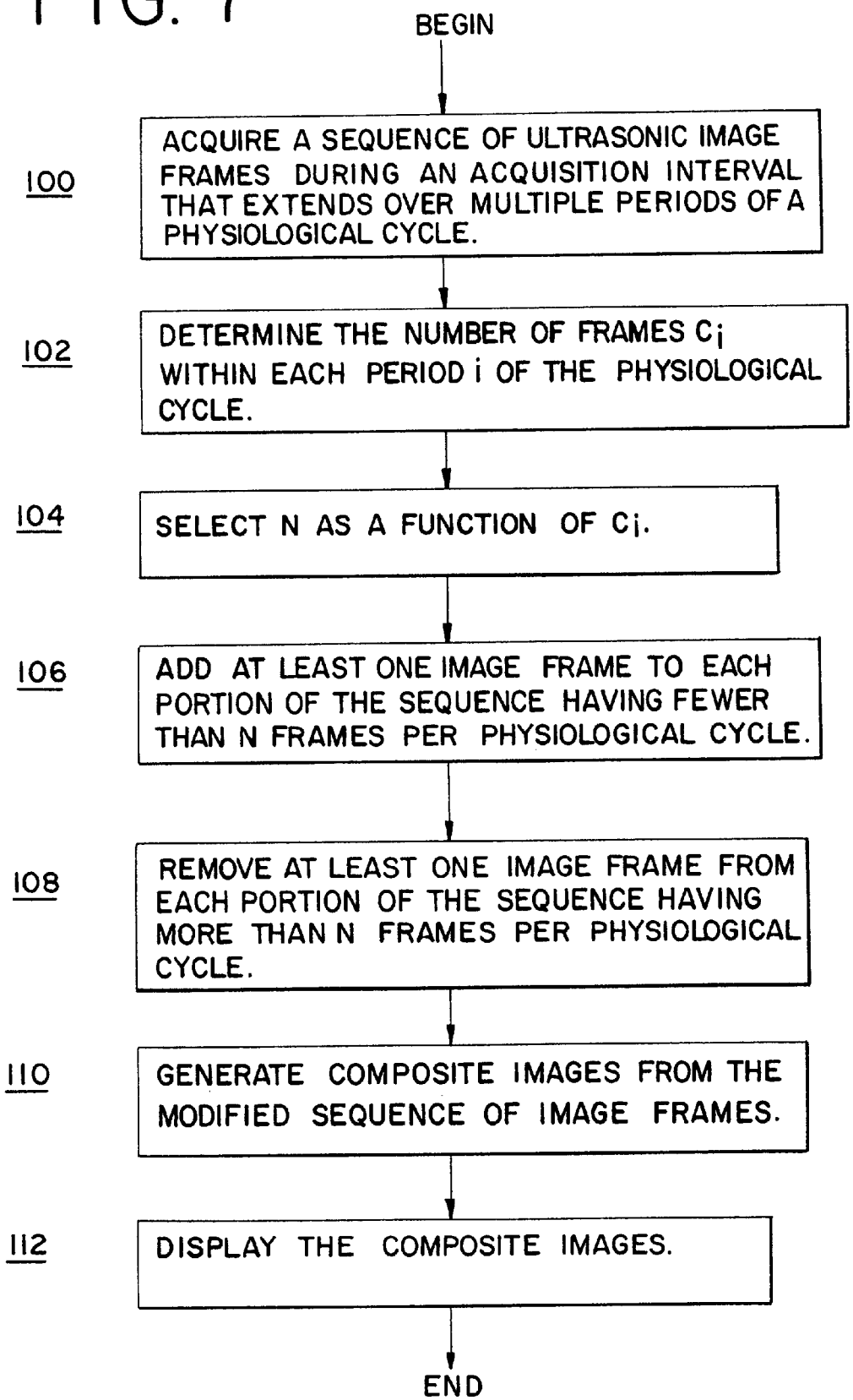
FIG. 7 is a flow chart of a method for generating a multiple image sequence, including a preferred method for synchronizing with image frames of the sequence.

FIG. 7 provides a flow chart of a preferred implementation of this method. In block 100, a sequence of ultrasonic image frames is acquired during an acquisition interval that extends over multiple periods of a physiological cycle. These image frames can be acquired using any of the techniques discussed above, using any suitable ultrasonic imaging system. Preferably, each of the ultrasonic image frames is time stamped with a respective acquisition time, and the interval between adjacent image frames is kept constant. For example, the sequence of the ultrasonic image frames may be acquired by slowly moving a transducer probe across the body of a patient, and each of the ultrasonic image frames may be acquired with positional information indicating the position and/or orientation of the transducer probe at the time the respective image frame was acquired.

Next, the number of image frames $C_i$ is determined within each period i of the physiological cycle. Many approaches can be used to determine the values of $C_i$ within each period of the physiological cycle, and one preferred approach is described below in conjunction with FIG. 8. Note that the values of $C_i$ will typically differ from one another due to irregularities in the physiological cycle, and due to the fact that the physiological cycle is in general not equal to an integer number of acquisition time periods. Next, an integer N is selected as a function of $C_i$. In various implementations, N can be set equal to the maximum value achieved by $C_i$, i.e. the maximum number of frames acquired within any single period of the physiological cycle. Alternatively, the integer N can be set to the minimum value of $C_i$, i.e. the minimum number of frames acquired during any single period of the physiological cycle. As yet another alternative, N can be set equal to any integer that is close or equal to the average value of $C_i$.

At 106 the integer value N is compared to each value of $C_i$. At least one image frame is added to each portion of the image frame sequence having fewer than N frames per physiological cycle. For example, if N is equal to 10, and one period of the physiological cycle contains only 9 image frames, another image frame is added such that the physiological cycle will contain 10 frames. The added frame can be formed in various ways. For example, the added frame or frames can simply be made equal to duplicates of adjacent frames. Alternatively, the added frame or frames may be interpolated from adjacent image frames. Preferably, the added frame is inserted into the sequence during a portion of the sequence characterized by low Doppler velocity values or low Doppler energy values. In general, the term "Doppler values" will be used for parameters such as Doppler velocity, Doppler energy, and other Doppler parameters indicative of tissue movement or blood flow.

At 108 at least one image frame is removed from each portion of the image frame sequence having more than N frames per physiological cycle. For example, a single frame of the sequence is removed from a portion of the sequence having eleven frames per physiological cycle, in the case where N equals 10 as described above. The image frame that is removed is preferably removed from a portion of the sequence characterized by low Doppler values.

At the conclusion of block 108 the modified image frame sequence includes N frames for each physiological cycle. These N frames are then taken as corresponding to N respective phases of the physiological cycle. In the example where N=10, the $n^{th}$ frame in the period of each physiological cycle is assigned a phase equal to 36(n−1) degrees. Thus, the first frame in each period is assigned the phase of 0°, and the tenth frame in each period is assigned the phase of 324°.

In block 110, composite images are generated from the sequence of image frames, using only image frames of the same phase (as determined above) within any given composite or multi-frame image. Any of the techniques described above can be used for registering and compositing the multi-frame images. For example, the multi-frame images can be three-dimensional images or two-dimensional, extended field of view images. The alignment techniques used for forming the multi-frame images can include any desired approach, including all of those discussed above. Also, various techniques can be used to measure the position of the transducer probe, and therefore the position and orientation of the respective image frames, including magnetic measuring systems, sonic measuring systems, and articulated joint measuring systems. The result of block 110 is a sequence of composite, multi-frame images, each characterized by a respective phase of the physiological cycle. The composite images are then displayed in block 112 as a time sequence of composite images. Preferably, the display rate used in block 112 is adjusted to match the estimated period of the physiological cycle.

The beginning of a physiological cycle can be defined in different ways. In a preferred embodiment, one can define the maximum Doppler velocity/energy in each physiological cycle as the beginning phase. In an alternative preferred embodiment, one can define the minimum Doppler velocity/energy in each physiological cycle as the beginning phase. Due to the fact that the first frame acquired may not be the beginning phase, and the last frame acquired may not be the last phase in a physiological cycle, the images in the first cycle and the images in the last cycle may be incomplete and not cover the entire cycle. For this reason, the total number of acquired images for each phase will often not be equal to the same number. When displaying the sequence of composite, multi-frame images, images are preferably displayed from the beginning phase to the end phase, and then the cycle is repeated. Preferably, if some phase images in the first or the last cycle are missing, these cycles are still used in generating the same-phase 3-D volume or 2-D extended field of view image. In this embodiment, the number of images that are used for each phase may be different. In another embodiment, if some phase images in the first or last cycle are missing, these cycles are not used in generating the same-phase 3-D or 2-D extended field of view image, so that the same number of images are assembled for each phase.

Figure 8:
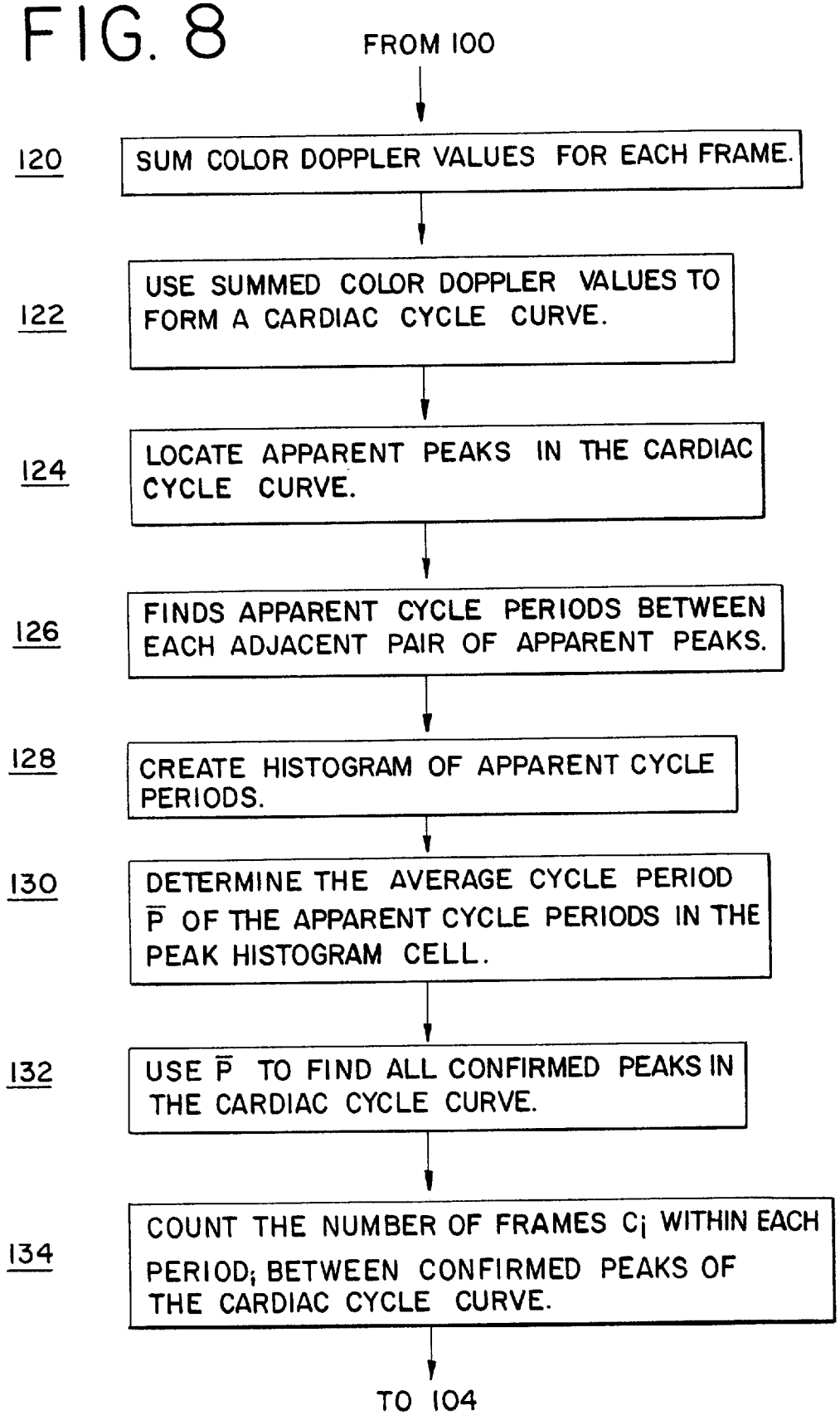
FIG. 8 is a flow chart providing more detail of one preferred implementation of block 102 of FIG. 7.
Figure 9:
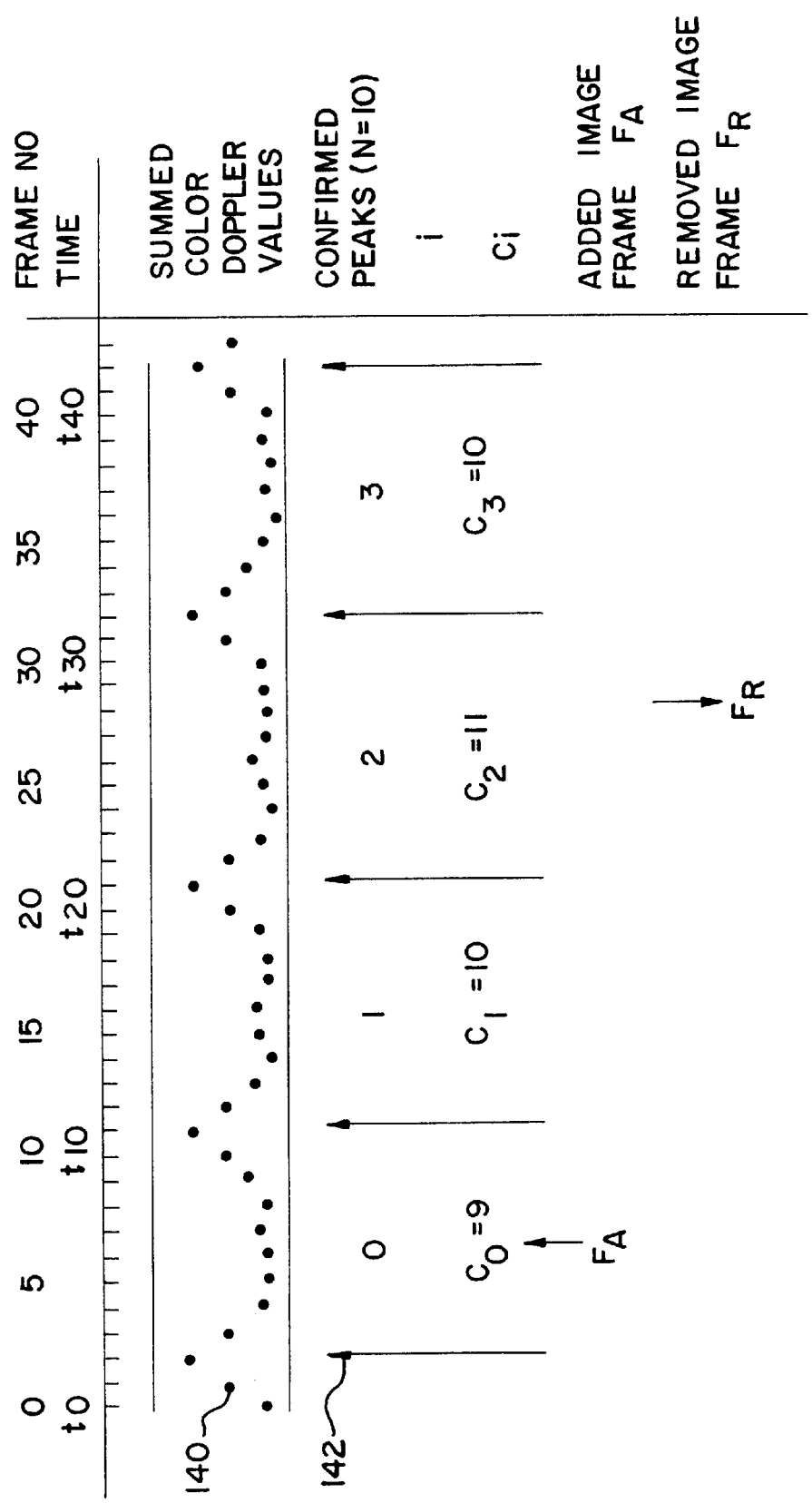
FIG. 9 is a time diagram illustrating operation of the methods of FIGS. 7 and 8.

FIGS. 8 and 9 provide further information for a preferred implementation of block 102 of FIG. 7. In FIG. 9, the first and second lines indicate the acquired frame numbers 0 through 43 and the respective time stamps $T_0$ through $T_{43}$.

In FIG. 8, first the color Doppler values are summed for each of the frames in block 120. This sum can be normalized for the number of color pixels. For example, by summing all energy levels for all color pixels of a Doppler flow velocity or Doppler flow energy frame, and then dividing by the number of color pixels, the mean Doppler value can be obtained for each frame. The third line of FIG. 9 shows the summed color Doppler values 140 for each of the frames 0 through 43. The example of FIG. 9 uses the cardiac cycle as the physiological cycle, and the summed color Doppler values 140 peak at a high-blood-flow portion of each period of the cardiac cycle.

Returning to FIG. 8, in block 124 apparent peaks are located in a cardiac cycle curve (formed by the summed color Doppler values 140 of FIG. 9). Next, at 126 the apparent cycle period is measured between each adjacent pair of apparent peaks in the cardiac cycle curve. As noted above, each value of the cardiac cycle curve is associated with a respective image frame having a respective time stamp. These time stamps are used in block 126 to determine the apparent cycle periods.

In block 128 a histogram is created of apparent cycle periods. That is, the apparent cycle periods are grouped in histogram cells, each cell representing cycle periods within a respective range of times. The histogram indicates how many apparent cycle periods fall within each of the histogram cells.

In block 130 the average cycle period $\overline{P}$ of the apparent cycle periods is determined from only the apparent cycle periods that are represented in the histogram cell having the most samples in the cell and neighbor cells within a predefined distance, namely the cluster radius. The cluster radius can be set as a percentage of the estimated number of frames in a physiological cycle. In one example, the scanning rate is 20 frames per second, and the estimated number of frames in one heart cycle is 20. If we take 5% of this number as the cluster radius, then the cluster radius equals 1 frame. This cell represents the biggest cluster of apparent cycle periods, i.e. the largest number of apparent cycle periods that are close to each other. The center of weight of all of the apparent cycle periods within this cluster is set equal to $\overline{P}$, which is taken as the best estimate of the true average cycle period. This approach allows false cardiac peaks located in block 124 to be ignored.

In block 132 $\overline{P}$ is used to find all confirmed peaks in the cardiac cycle curve. A confirmed peak is found by first finding the apparent cardiac cycle peak that has two adjacent cardiac cycle periods from this peak that are most closely equal to $\overline{P}$. All confirmed peaks are found with reference to this first confirmed peak, guided by the average cardiac cycle period $\overline{P}$. For example, starting with the first confirmed cardiac cycle peak, an offset equal to $\overline{P}$ is used to find a next local maximum of the cardiac cycle curve within a small search range. This local maximum is taken as the next confirmed cardiac cycle peak, and the process is repeated, starting with the most recently confirmed cardiac cycle peak. FIG. 9 shows four confirmed cardiac cycle peaks 142, labeled 0 through 3.

At 134 the number of frames $C_i$ is counted within each period i between confirmed peaks of the cardiac cycle curve. In FIG. 9, values of $C_0$ though $C_3$ are shown. FIG. 9 also shows the manner in which a frame $F_a$ is added during period 0 ($C_0$=9<10). Note that the added frame $F_a$ is inserted between frames 6 and 7, during a slowly moving portion of the cardiac cycle (e.g., low Doppler velocity or Doppler energy). Similarly, FIG. 9 shows that an image frame $F_r$ is removed from the second period ($C_2$=11>10). In this case frame 28 is removed, also from a slowly moving portion of the cardiac cycle.

Table 1 shows the resulting modified sequence of image frames and the associated phase angles. Note that the desired synchronization has been achieved.

TABLE 1

| Phase Angle of Modified Frame Sequence | | | | | | | | | | |
|---|---|---|---|---|---|---|---|---|---|---|
| 0° | 36° | 72° | 108° | 144° | 180° | 216° | 252° | 288° | 324° | Phase Angle |
|  |  |  |  |  |  |  |  | 0 | 1 | FRAME NUMBER |
| 2 | 3 | 4 | 5 | 6 | $F_A$ | 7 | 8 | 9 | 10 | (Period 0) |
| 11 | 12 | 13 | 14 | 15 | 16 | 17 | 18 | 19 | 20 | (Period 1) |
| 21 | 22 | 23 | 24 | 25 | 26 | 27 | 29 | 30 | 31 | (Period 2) |
| 32 | 33 | 34 | 35 | 36 | 37 | 38 | 39 | 40 | 41 | (Period 3) |
| 42 | 43 |  |  |  |  |  |  |  |  |  |

Because the added frames $F_a$ are added and the removed frames $F_r$ are removed during portions of the cardiac cycle that are both low in velocity (or energy) and slowly changing, visual impact is minimized.

Many variations are possible. For example, instead of duplicating or discarding frames near the middle of the cardiac cycle between cardiac peaks, the frame number can be interpolated or down sampled to the ideal frame number, thereby causing some frames to be used more than once. The cardiac cycle can be determined with reference to minimums as opposed to maximums of the physiological cycle curve.

Interpolated frames can be used instead of repeating or discarding frames. Interpolated frames require greater computational resources, and they may not be needed in many applications.

The image frames can be of any desired modality. For example, color Doppler velocity, energy, and variance (and any combination thereof) can be used. Similarly, B-mode image frames can be used. The imaging mode can be fundamental imaging or harmonic imaging (tissue or agent), or combinations thereof.

This invention is not limited to use with any particular type of system for acquiring ultrasonic image frames, ultrasonic image frames of any particular type or modality, or any specific technique for creating multi-frame images, whether two or three dimensional. As pointed out above, the position and orientation of the individual image frames may either be measured by an external system or derived from image information.

The cluster searching method described above can be used in many applications, and it is not limited to use in systems for creating composite images. In general, the cluster method is useful in searching a physiological cycle such as the cardiac cycle to determine a selected phase of the cycle. For example, the cluster method can be used in a radiology ultrasound platform as a robust method for locating a selected phase such as a peak of the cardiac cycle. As described above, the average cardiac cycle period is determined using the cluster method described above, and then a search is performed based on this average cardiac cycle period to locate confirmed peaks of the cardiac cycle.

Depending upon the application, the physiological cycle signal may be generated in many ways, and it is not limited to the Doppler techniques described above. For example, the physiological cycle signal analyzed with the cluster method described above may be derived from image motion measurements, image position measurements, or non-image signals.

As used herein, the term "multi-frame" as applied to a data set or an image means that data from two or more separate frames contribute to the data set or image. Though possible, it is not required that two or more entire frames contribute to the data set or image.

It should be apparent from the foregoing that a dynamic, multi-frame image display has been described which exhibits the advantages of three-dimensional imaging or extended field of view imaging in combination with the ability to acquire and present data from a sequence of phases of the selected physiological cycle.

The foregoing detailed description has described only a few of the many forms that this invention can take. For this reason this detailed description is intended by way of illustration and not by way of limitation. It is only the following claims, including all equivalents, that are intended to define the scope of this invention.

What is claimed is:

1. A medical ultrasonic imaging method for generating a multiple image sequence, said method comprising:
    (a) acquiring a sequence of medical ultrasonic image frames during an acquisition interval that extends over multiple periods of a physiological cycle, said sequence comprising $C_i$ frames in each $i^{th}$ period of the physiological cycle;
    (b) selecting an integer N based on at least some of the values of $C_i$;
    (c) performing at least one act selected from the group consisting of:
        (i) adding at least one image frame to a portion of the sequence characterized by fewer than N frames per physiological cycle; and
        (ii) removing at least one image frame from a portion of the sequence characterized by more than N frames per physiological cycle.

2. The method of claim 1 wherein the integer N selected in (b) is indicative a maximum one of said at least some of the values of $C_i$.

3. The method of claim 1 wherein the integer N selected in (b) is indicative of a minimum one of said at least some of the values of $C_i$.

4. The method of claim 1 wherein the integer N selected in (b) is indicative of a function of said at least some of the values of $C_i$ selected from the group consisting of: an average, a median, and combinations thereof.

5. The method of claim 1 wherein the integer N selected in (b) is indicative of a function of said at least some of the values of $C_i$ selected from the group consisting of: a maximum and a minimum.

6. The method of claim 1 wherein (c)(i) comprises adding the at least one image frame at a location in the sequence corresponding to a slowly-moving portion of the physiological cycle.

7. The method of claim 1 wherein (c)(ii) comprises removing the at least one image frame at a location in the sequence corresponding to a slowly-moving portion of the physiological cycle.

8. The method of claim 1 wherein the at least one image frame added in (c)(i) is a duplicate of another of the image frames of the sequence.

9. The method of claim 1 wherein the at least one image frame added in (c)(i) is interpolated from selected image frame of the sequence.

10. The method of claim 1 wherein (b) comprises:
    (b1) acquiring a physiological cycle signal that is time coordinated with the sequence of image frames;
    (b2) locating a plurality of values of the physiological cycle signal that appear to correspond to a selected phase of the physiological cycle;
    (b3) determining a plurality of cycle period values based on the signal values located in (b2);
    (b4) determining a cluster of the cycle period values determined in (b3);
    (b5) determining a parameter as a function of the cluster of the cycle period values determined in (b4); and
    (b6) determining the integer N based on the parameter determined in (b5).

11. The method of claim 10 wherein the selected phase of (b2) corresponds to peaks of the physiological cycle signal.

12. The method of claim 10 wherein (b1) comprises forming the physiological cycle signal based on summed color Doppler values of the respective image frames.

13. The method of claim 10 wherein the mathematical function of (b5) is selected from the group consisting of: an average, a median, and combinations thereof.

14. The method of claim 10 wherein the mathematical function of (b5) is selected from the group consisting of: a maximum and a minimum.

15. The method of claim 1 further comprising:
    (d) generating a plurality of composite images from the image sequence of image frames after (c), each composite image comprising image information from at least two of the image frames associated with a respective phase of the physiologic cycle; and
    (e) displaying the composite images.

16. The method of claim 15 further comprising:
    (f) adjusting a display frame rate in (e) based on the integer N.

17. A medical ultrasonic imaging method for determining an average cycle period for a sequence of ultrasonic image frames, said method comprising:
    (a) acquiring a physiological cycle signal that is time coordinated with the sequence of image frames;
    (b) locating a plurality of values of the physiological cycle signal that appear to correspond to a selected phase of the physiological cycle;

(c) determining a plurality of cycle period values based on the signal values located in (b);

(d) determining a cluster of the cycle period values determined in (c); and (e) determining an average cycle period based on the cluster determined in (d).

18. The method of claim 17 wherein (a) comprises forming the physiological cycle signal based on summed color Doppler values of the respective image frames.

19. A method for locating a selected phase of a physiological cycle, said method comprising:

(a) acquiring a physiological cycle signal;

(b) locating a plurality of values of the physiological cycle signal that appear to correspond to a selected phase of the physiological cycle;

(c) determining a plurality of cycle period values based on the signal values located in (b);

(d) determining a cluster of the cycle period values determined in (c); and (e) determining an average cycle period based on the cluster determined in (d).

20. The method of claim 17 or 19 wherein the selected phase of (b) corresponds to peaks of the physiological cycle signal.

21. The method of claim 17 or 19 further comprising:

(f) locating a plurality of values of the physiological cycle signal that are separated by the average cycle period of (e).

* * * * *